US00RE40116E

(19) United States
(12) Reissued Patent
Engstrom

(10) Patent Number: US RE40,116 E
(45) Date of Reissued Patent: Feb. 26, 2008

(54) MOBILE DIGITAL COMMUNICATION COMPUTING DEVICE INCLUDING HEART RATE MONITOR

(76) Inventor: G. Eric Engstrom, 12415 Holmes Pt. Dr. NE., Kirkland, WA (US) 98033

(21) Appl. No.: 11/108,153

(22) Filed: Apr. 15, 2005

Related U.S. Patent Documents

Reissue of:
(64) Patent No.: 6,549,756
Issued: Apr. 15, 2003
Appl. No.: 09/690,679
Filed: Oct. 16, 2000

(51) Int. Cl.
*H04B 7/00* (2006.01)

(52) U.S. Cl. ..... 455/66.1; 455/575.1; 455/90.1; 455/100; 455/566; 455/128; 455/351; 600/509; 600/513; 600/519

(58) Field of Classification Search ..... 455/66.1, 455/575.1, 90.1, 90.2, 90.3, 100, 128, 351; 600/508–528; 128/904, 905
See application file for complete search history.

(56) References Cited

U.S. PATENT DOCUMENTS 4,320,767 A * 3/1982 Villa-Real ..... 600/493
4,625,732 A * 12/1986 Kasa et al. ..... 128/905 X
4,867,442 A * 9/1989 Matthews ..... 600/502 X
4,938,228 A * 7/1990 Righter et al. ..... 600/503
5,670,944 A * 9/1997 Myllymaki ..... 340/573.1
5,827,179 A * 10/1998 Lichter et al. ..... 600/481 X
6,100,806 A * 8/2000 Gaukel ..... 340/573.4
6,790,178 B1 * 9/2004 Mault et al. ..... 600/508 X

* cited by examiner

*Primary Examiner*—Philip J. Sobutka
(74) *Attorney, Agent, or Firm*—Schwabe, Williamson & Wyatt, P.C.

(57) ABSTRACT

A mobile client device, such as a wireless mobile or a palm sized personal digital assistant, is provided with a number of sensors and companion programming instructions/circuitry to generate a heart rate reading for a user holding the device. The sensors are used to sense blood flow rate of the user. The sensors are advantageously disposed in a distributed manner, in a number of locations of the mobile client device. The programming instructions/circuitry are used to infer a holding pattern of the device, and generate the heart rate reading, using a subset of the sensed data, based at least in part on the inferred holding pattern.

39 Claims, 7 Drawing Sheets

MOBILE DIGITAL COMMUNICATION COMPUTING DEVICE INCLUDING HEART RATE MONITOR

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to the fields of mobile communication and/or computing devices. More specifically, the present invention relates to the incorporation of bio-metric sensors/monitors in these devices.

2. Background Information

Advances in computer and telecommunication technology have led to wide spread adoption of mobile client devices, from the basic wireless telephones to function rich notebook sized computers that pack the power of a desktop computer. In between are web enabled wireless telephones, palmed sized personal digital assistants (PDA) and so forth. As a result, professionals are virtually always only a few clicks or buttons away from their home offices.

While these capabilities have increased the mobility of modern professionals, they also have contributed to longer work hours and increased stress for the professionals. However, as society in general becomes more health conscious, notwithstanding their busy work schedules, more and more professionals are allocating time to exercise or participate in physical activities. This trend has not gone unnoticed to the application developers, which as a result have become increasingly interested in incorporating bio-metric data in their applications.

Among the modern mobile client devices, unquestionably, wireless mobiles and palm sized PDAs have emerged as the two most popular mobile client devices for modern professionals. Thus, increasingly, artesian are interested in being able to collect bio-metric data using these devices.

SUMMARY OF THE INVENTION

A mobile client device, such as a wireless mobile phone or a palm sized personal digital assistant, is provided with a number of sensors and companion programming instructions/circuitry to generate a heart rate reading for a user holding the device. The sensors are used to sense blood flow rate of the user. The sensors are advantageously disposed in a distributed manner, in a number of locations of the mobile client device, to allow collection of multiple blood flow rate readings of the user. The programming instructions/circuitry are used to infer a holding pattern of the device, and generate the heart rate reading using a subset of the sensed data, based at least in part on the inferred holding pattern.

In one embodiment, the sensors are distributively disposed along two edges of the mobile client device, to facilitate collection of blood flow rate data for at least a left hand holding pattern and a right hand holding pattern. In one embodiment, the holding pattern is inferred by comparing the sensed data with one or more reference characteristic profiles. In one embodiment, a set of weights is also selected to normalize the employed sensed data.

BRIEF DESCRIPTION OF DRAWINGS

The present invention will be described by way of exemplary embodiments, but not limitations, illustrated in the accompanying drawings in which like references denote similar elements, and in which.

DETAILED DESCRIPTION OF THE INVENTION

In the following description, various aspects of the present invention will be described. However, it will be apparent to those skilled in the art that the present invention may be practiced with only some or all aspects of the present invention. For purposes of explanation, specific numbers, materials and configurations are set forth in order to provide a thorough understanding of the present invention. However, it will also be apparent to one skilled in the art that the present invention may be practiced without the specific details. In other instances, well known features are omitted or simplified in order not to obscure the present invention.

Parts of the description will be presented using terms such as end-users interfaces, buttons, and so forth, commonly employed by those skilled in the art to convey the substance of their work to others skilled in the art. Parts of the description will be presented in terms of operations performed by a computing device, using terms such as sensing, converting, comparing, storing, generating and so forth. As well understood by those skilled in the art, these quantities and operations take the form of electrical, magnetic, or optical signals capable of being stored, transferred, combined, and otherwise manipulated through mechanical and electrical components of a digital system. The term digital system includes general purpose as well as special purpose computing machines, systems, and the like, that are standalone, adjunct or embedded.

Various operations will be described in turn in a manner that is most helpful in understanding the present invention, however, the order of description should not be construed as to imply that these operations are necessarily order dependent. Furthermore, the phrase "in one embodiment" will be used repeatedly, however the phrase does not necessarily refer to the same embodiment, although it may.

Figure 1:
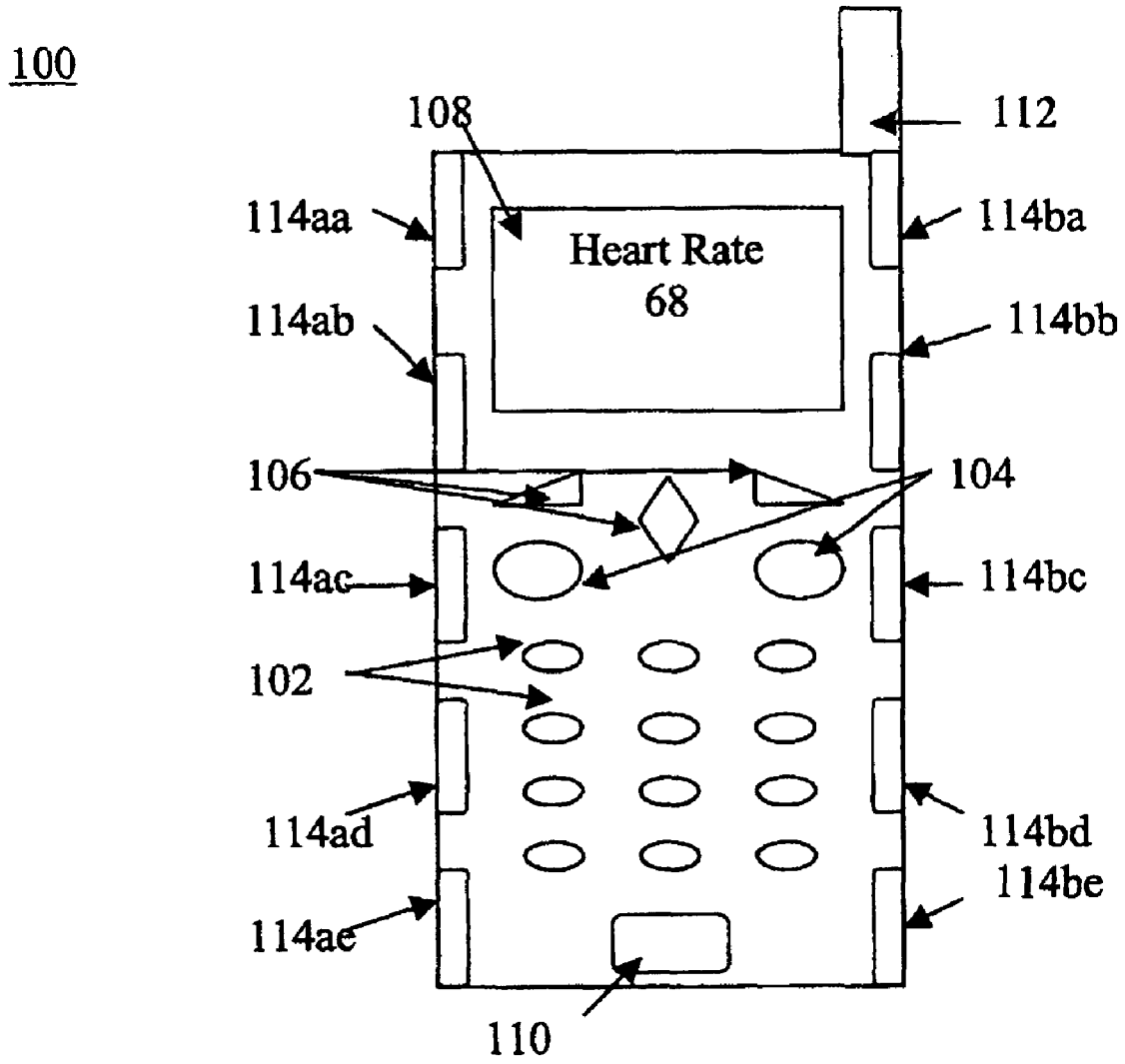
FIG. 1 illustrates a front view of a wireless mobile phone incorporated with heart rate sensors in accordance with one embodiment.

Referring now to FIG. 1, wherein a front view of a wireless mobile phone, incorporated with the teachings of the present invention, in accordance with one embodiment, is shown. As illustrated, similar to a conventional wireless mobile phone, wireless mobile phone 100 includes key pad 102, "talk" and "end talk" buttons 104, cursor control buttons 106, display screen 108 and antenna 112. However, unlike prior art wireless mobile phones, wireless mobile phone 100 is equipped with a number of sensors 114aa–114ae and 114ba–114be to sense a number of blood flow rate readings of a user holding wireless mobile phone 100. Wireless mobile phone 100 is also provided with either companion programming instructions or circuitry (or combination thereof to generate a heart rate reading for the user using the data sensed by sensors 114aa–114ae and 114ba–114be.

In accordance with the present invention, sensors 114aa–114ae and 114ba—114be are advantageously disposed in a distributed manner, at a number of locations of wireless mobile phone 100. For the illustrated embodiments, sensors 114aa–114ae and 114ba–114be are distributively disposed along the two side edges of wireless mobile phone 100. As a result, the blood flow rate of the user may be sensed at multiple points, more importantly, at different combinations of these points, depending one how mobile phone 100 is held by the user.

For example, if mobile phone 100 is held in a left hand position, the user's thumb and the lower left region of the user's palm are more likely to be in contact with sensors 114aa, 114ad and 114ae, giving three reasonably accurate readings of the user's blood flow rate, while sensors 114ab and 114ac most likely will not make very good contact with the user's palm or fingers, yielding unreliable readings of the user's blood flow rate. At the same time, the user's remaining four fingers are more likely to be in contact with sensors 114ba–114bd, yielding reliable readings, with sensor 114be most likely not making very good contact with the user's palm or fingers, yielding unreliable readings. On the other hand, if mobile phone 100 is held in a right hand position, the user's thumb and the lower right region of the user's palm are more likely to be in contact with sensors 114ba, 114bd and 114be, yielding more reliable readings, with sensors 114bb and 114bc most likely not making very good contact with the user's palm or fingers, yielding unreliable readings. At the same time, the user's remaining four fingers are more likely to be in contact with sensors 114aa–114ad, yielding reliable readings, with sensor 114ae most likely not making very good contact with the user's palm or fingers, yielding unreliable readings.

Thus, it can be seen, a user holding pattern (of the mobile phone 100) can be inferred from the relative strength of the sensing signals generated by the distributively disposed sensors 114aa–114ae and 114ba–114be. The companion programming instructions/circuitry are designed to do just that, i.e. infer the holding pattern based on the relative strength of the sensing signals. In one embodiment, the companion programming instructions/circuitry make the inference using reference characteristic profiles, to be described more fully below. In turn, the companion programming instructions/circuitry generate the heart rate reading using a subset of the sensing data, based at least in part on the inferred holding pattern. In one embodiment, the employed sensed data are also "normalized" to reflect the different strength a user may employ in holding mobile phone 100.

For the illustrated embodiment, mobile phone 100 also includes a dedicated service request button 110 to allow the roving user to request for services from different locations or have location information of the user be selectively providing to various recipients. Requesting for service by a roving user is the subject of co-pending U.S. Patent Application, <number to be assigned>, entitled "Method and Apparatus for Roving Request for Service", filed contemporaneously, and having at least partial common inventorship with the present application. Selective provision of location information of the user to various recipients is the subject matter of co-pending U.S. Patent Application, <number to be assigned>, entitled "Method and Apparatus for People to Simply Communicate Their Location and Activity, also filed contemporaneously, and having at least partial common inventorship with the present application. Except for the recursive incorporation, both of these applications are hereby fully incorporated by reference.

Figure 2:
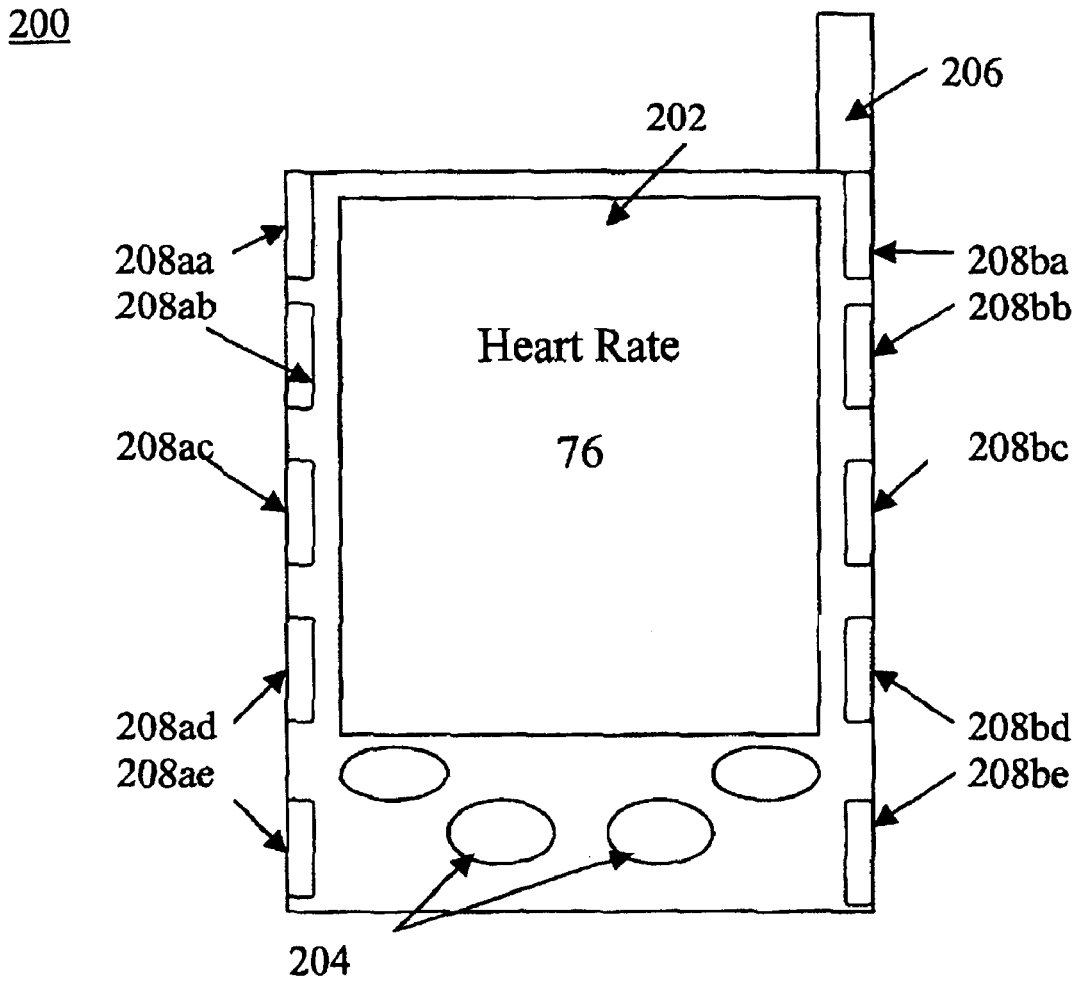
FIG. 2 illustrates a front view of a palm sized PDA incorporated with heart rate sensors in accordance with another embodiment.

FIG. 2 illustrates a front view of a palm sized PDA, incorporated with the teachings of the present invention, in accordance with one embodiment. As illustrated, similar to a conventional PDA, PDA 200 includes display screen 202, function buttons 204, and antenna 206. However, unlike prior art PDA, but similar to wireless mobile phone 100, PDA 200 is equipped with a number of sensors 208aa–208ae and 208ba—208be to sense the blood flow rate of a user holding PDA 200. Also similar to wireless mobile phone 100, PDA 200 is also provided with either programming instructions or circuitry (or combination thereof) to generate a heart rate reading for the user, using the data sensed by sensors 208aa–208ae and 208ba–208be.

As wireless mobile phone 100, sensors 208aa–208ae and 208ba–208be are advantageously disposed in a distributed manner, at a number of locations of PDA 200. For the illustrated embodiments, sensors 208aa–208ae and 208ba–208be are distributively disposed along the two side edges of PDA 200. As a result, the blood flow rate of the user may also be sensed at multiple points, more importantly, at different combinations of these points, depending on how PDA 200 is held by the user. As described earlier, the companion programming instructions/circuitry are designed to infer the holding pattern based on the relative strength of the sensing signals. In turn, the companion programming instructions/circuitry generate the heart rate reading using a subset of the sensing data, based at least in part on the inferred holding pattern.

Similar to mobile phone 100, PDA 200 may be equipped with a roving request for service application or a location information distribution application. If so, a service request or location information distribution "home" page may be retrieved from a messaging service, and rendered on display screen 202. The service request/location information distribution "home" page may include a "drop down" menu of services available for request, request button, current location and status display. As a result, a user of PDA 200 may also request anyone of the services included in the "drop down" menu, such as calling a taxi, ordering a take out, buying some local wines, and the like, or request the user's current location information being provided to a number of selected recipients, such as the user's parent, friends, and so forth, as described in the co-pending incorporated by reference application.

Figure 3:
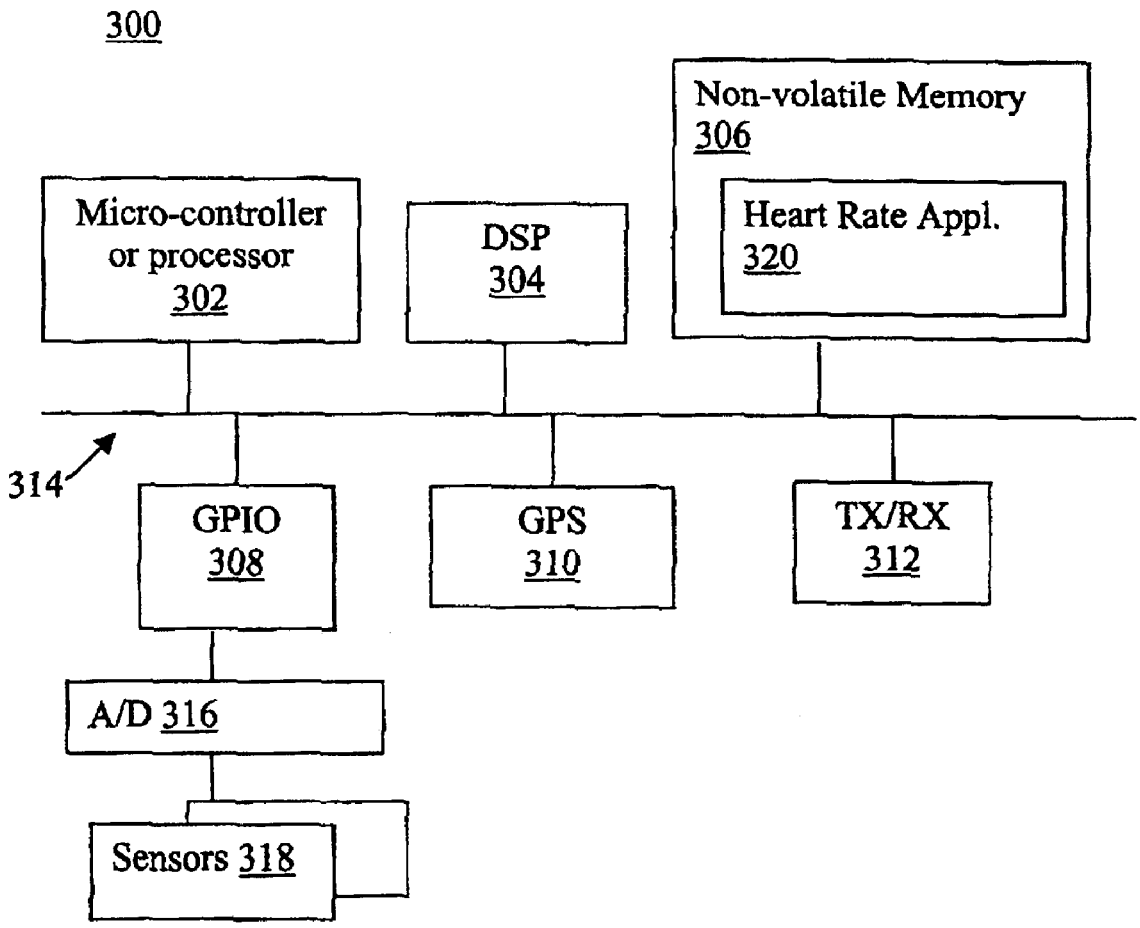
FIG. 3 illustrates an architectural view of the wireless mobile phone and the PDA of FIG. 1–2, in accordance with one embodiment.

FIG. 3 illustrates an architecture view of a mobile client device 300, which is intended to be representative of mobile phone 100 and PDA 200, in accordance with one embodiment. As illustrated, mobile client device 300 includes elements found in conventional mobile client devices, such as micro-controller/processor 302, digital signal processor (DSP) 304, non-volatile memory 306, general purpose input/output (GPIO) interface 308, and transmit/receive (TX/RX) 312. For the illustrated embodiment, mobile client device 300 also advantageously includes geographic positioning system 310, which is equipped to provide a user of mobile client device 300 his/her current location. [However, the provision of GPS 310, which desirable, is not essential to the practice of the present invention.] Further, mobile client device 300 is provided with sensors 318 (representative of earlier described sensors 114aa–114ae and 114ba–114be and sensors 208aa–208ae and 208ba–208be), A/D converter 316, and heart rate application 320 incorporated with the teachings of the present invention.

Selected ones of sensors 318 (depending a user's holding pattern) make contact with the user's palm or fingers, and generate electrical signals proportional to the blood flow rate detected by the sensors. Anyone of a number of such known sensors may be employed. A/D converter 316 converts the analog electrical signals into digital data. Similarly, anyone of a number of such known A/D converters may be employed. Heart rate application 320 in turn infers the holding pattern, and generate the heart rate accordingly, to be described more fully below. In alternate embodiments, in lieu of heart rate application 320, mobile client device 300 may be provided with dedicated circuitry for performing the holding pattern inference and heart rate generation operations (also to be described in more details below, referencing FIG. 7).

Except for the distributive employment of the sensors, and heart rate generation application 320 (or its circuitry equivalent), the functions and constitution of the various enumerated elements of FIG. 3 are known in the art, accordingly will not be otherwise further described either.

Figure 4:
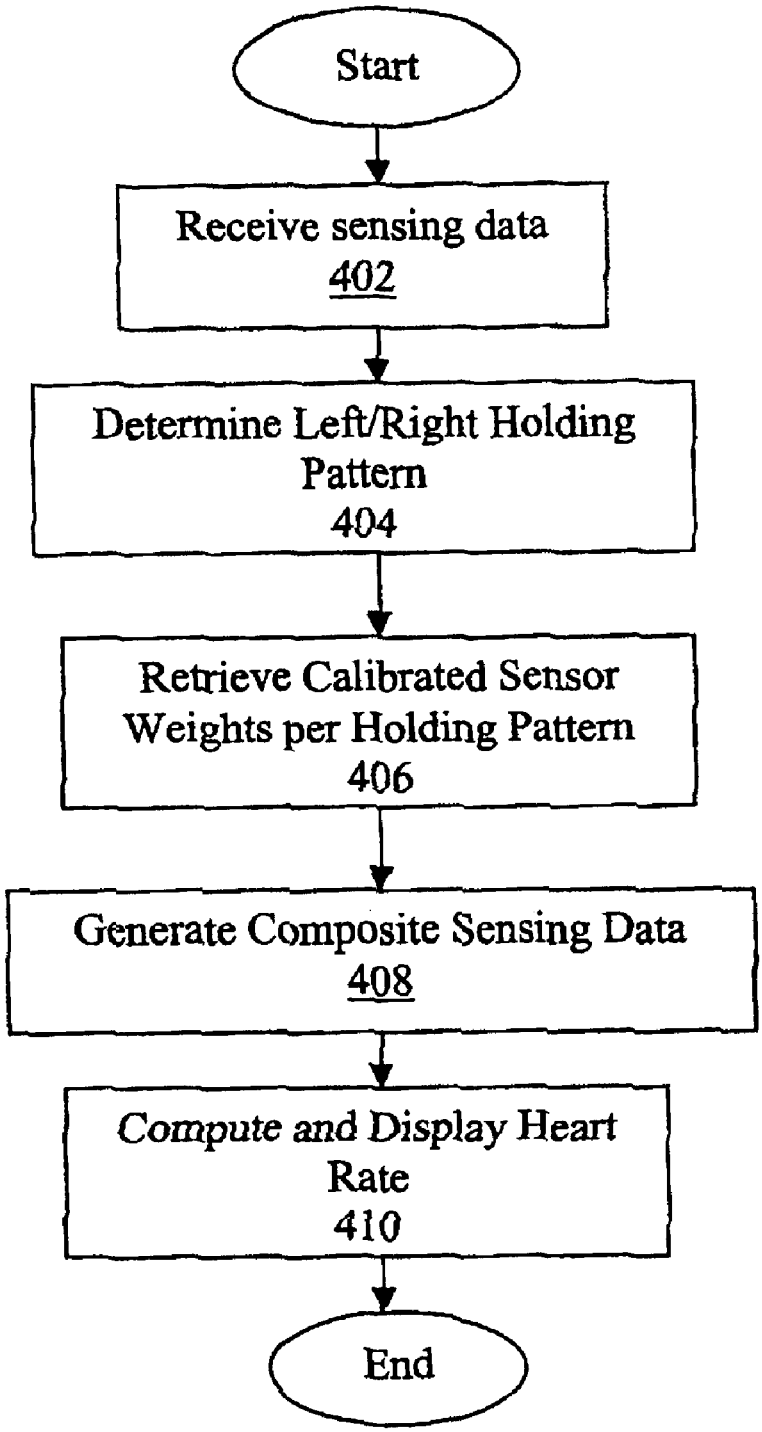
FIGS. 4–5 illustrate the operational flow of the relevant aspects of the heart rate application of FIG. 3, in accordance with one embodiment.

FIG. 4 illustrates the operational flow of the relevant aspects of the heart rate application of the present invention, in a normal mode of operation, in accordance with one embodiment. As illustrated, at block 402, heart rate application 320 receives sensing data from the distributively disposed sensors. At block 404, heart rate application 320 examines the received sensing data and infers a holding pattern of the mobile client device. In one embodiment, heart rate application 320 infers at least whether the mobile client device is being held by the user in a left hand or a right hand position. As alluded earlier, in one embodiment, heart rate application 320 makes the determination by comparing the received sensing data against a number of reference characteristic profiles, depicting the sensing signal characteristics for typical users holding the mobile client device with their left or right hands. [Recall that different sensors are expected to have "lower strength" sensing signals for different holding patterns.] At block 406, for the illustrated embodiment, heart rate application 320 further loads a set of calibrated weight corresponding to the determined holding pattern to normalize the subset of sensing data to be used (to reflect the different pressures different users may applied to the sensors when holding the mobile client device). [Recall from earlier description that the unused sensing data are the data generated by sensors that are not expected to make good contact with the user for the particular holding pattern.] At block 408, heart rate application 320 generates a composite signal, averaging the normalized sensing data. In alternate embodiments, other factors may also be employed to "smooth" the sensing data. At block 410, heart rate application 320 generates the heart rate reading based on the composite averaged reading (i.e. converting the measured flow rate represented by the signal rate into heart rate).

Figure 5:
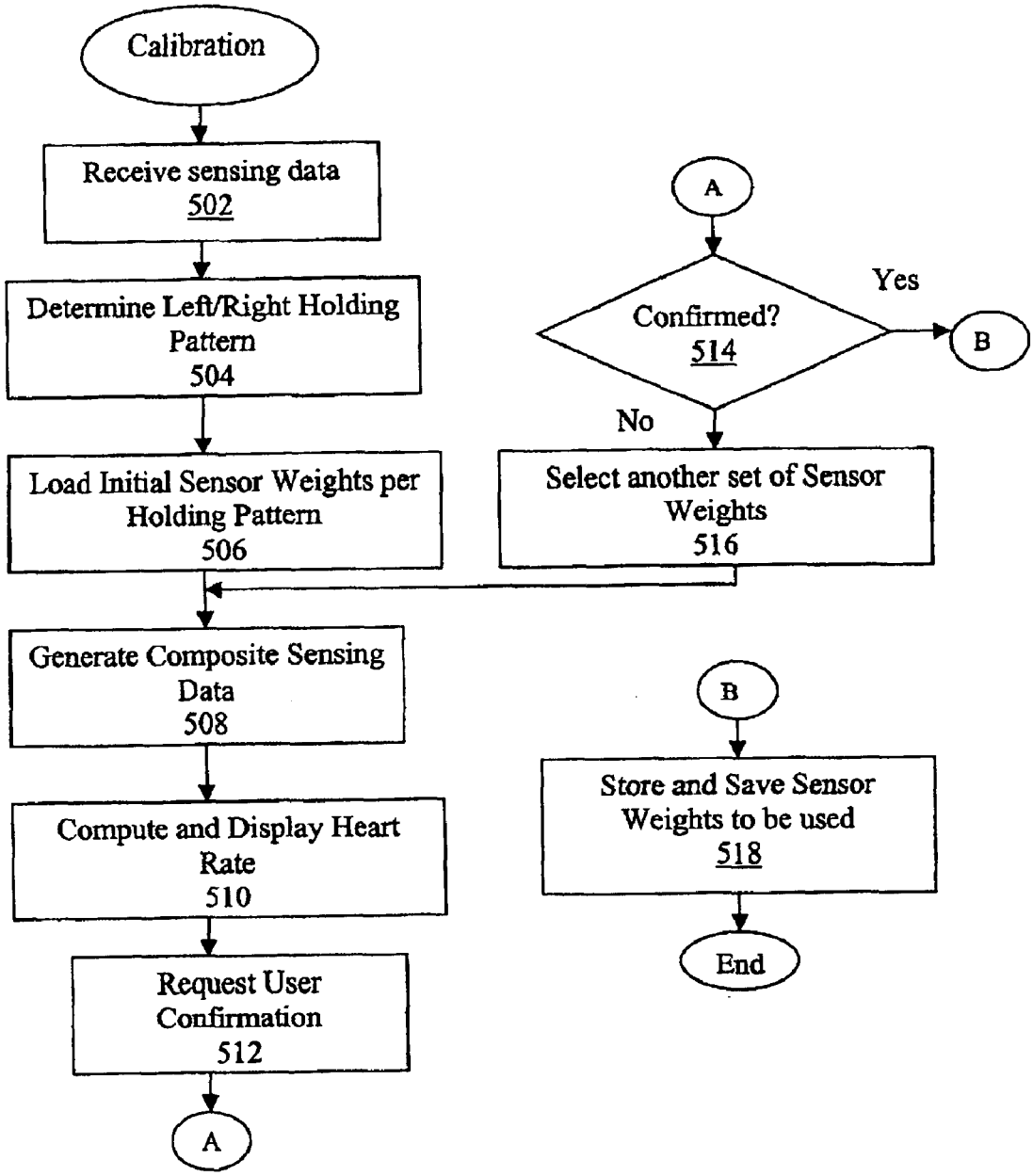

FIG. 5 illustrates the operational flow of the relevant aspects of the heart rate application of the present invention, in a calibration mode of operation, in accordance with one embodiment. At blocks 502–510, heart rate application 320 essentially performs the same operations as earlier described for blocks 402–410, when operating in the normal mode, except in block 506, in lieu of loading a calibrated set of weight as in the case of block 406, heart rate application 320 loads an initial set of "trial" weights. At block 512, heart rate application 320 asks the user to confirm if the generated reading using the "trial" weights to normalize the sensing data appear to be sufficiently accurate. The present invention contemplates that the user has a second independent method of learning about the user's heart rate, to allow the user to calibrate the present invention. At block 514, heart rate application 320 determines if the user confirms the computed heart rate using the "trial" weights is "sufficiently" accurate. If it is not, heart rate application 320 fetches another set of "trial" weights, and re-performs blocks 508–512. The process continues until eventually the user confirms that the generated heart rate is sufficiently accurate. At such time, heart rate application 320 saves the last set of "trial" weights as the "calibrated" weights for the particular holding pattern. The process may be repeated for different holding patterns. Further, in alternate embodiments, in lieu to loading different sets of "trial" weights, the initial set of "trial" weight may be systematically altered (i.e. increased or deceased) to locate the optimal normalization weights.

Figure 6:
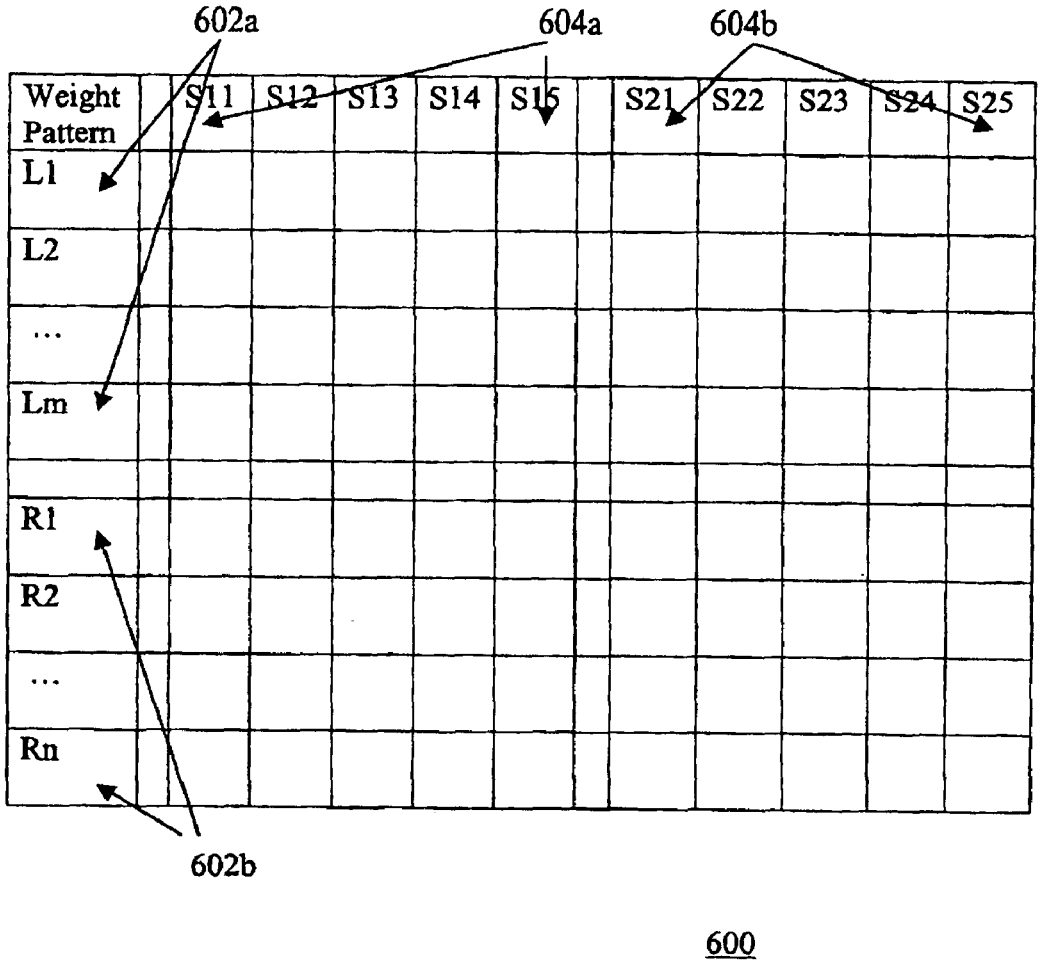
FIG. 6 illustrates an example data structure suitable for use to store the weight data associated with generating the heart rate for practicing the present invention, in accordance with one embodiment.

FIG. 6 illustrates a data structure suitable for use to store the weight data for practicing of the present invention. As illustrated, table 600 includes a number of weight sets for left hand holding patterns 602a and a number of weight sets for right hand holding patterns 602b. Each weight set 602a or 602b, includes a number of weights 604a for left side sensors 114aa–114ae or 208aa–208ae, and a number of weights 604b for right side sensors 114ba–114be or 208ba–208be. In one embodiment, once calibrated, the "optimal" weight set identifiers for the left and right hand holding patterns are saved in a working area or alternatively, in a configuration register.

Figure 7:
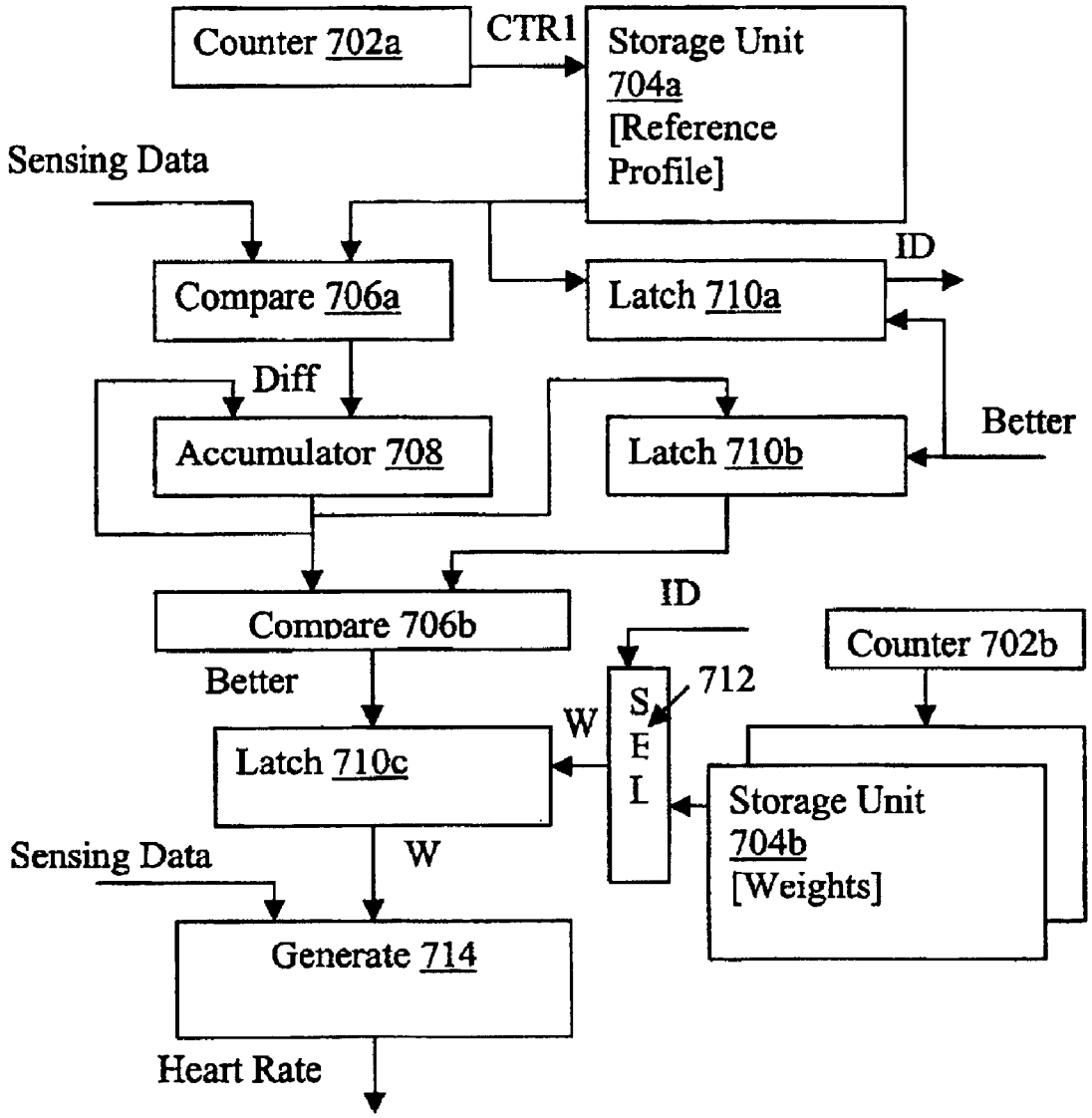
FIG. 7 illustrates a block diagram view of a circuit suitable for use to practice the present invention, in accordance with one embodiment.

FIG. 7 illustrates a block diagram view of an equivalent circuitry suitable for use to practice the present invention, in accordance with one embodiment. Circuitry 700 comprises counters 702a–702b, storage units 704a–704b, comparators 706a–706b, accumulator 708, latches 710a–710c, selector 712 and generator 714, coupled to each other as shown. Counter 702a is used to generate a pointer to storage units 704a to cause storage units 704a to output a reference sensing data characteristic profile. Comparator 706a compares the sensing data to the reference characteristic profile. Accumulator 708 accumulates the differences between the sensing data and reference data. Comparator 706b determines if the accumulated difference is smaller than the previously known smallest accumulated difference. If not, after a pre-determined number of clocks, counter 702a advances, causing another reference characteristic profile to be output for analysis. Eventually, after a predetermined number of trials or upon convergence towards a "best fit" reference characteristic profile, the "best" difference is latched into latch 710b, and the identifier of the characteristic profile is latched into latch 710a.

Thereafter, in like manner, counter 702b successively generates a series of pointers to cause different weight sets to be successively output for different holding patterns for analysis. Latched identifier of the most "fitting" reference characteristic profile causes selector 712 to select the appropriate trial weight sets corresponding to the inferred holding pattern to be examined. The selected trial weight set is then latched and used to normalized the sensing data, and upon normalization, compute the heart rate.

The computed heart rate may then be presented to the user for confirmation. The process may be repeated if necessary. Eventually, upon confirmation, the calibrated weight set may then be used during normal mode of operation.

Accordingly, a mobile client device having integrated capabilities for also generating a heart rate reading for a user holding the mobile client device has been described. While the present invention has been described in terms of the above illustrated embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A wireless mobile phone comprising:

a palm-sized body;

a transceiver for transmitting and receiving signals, disposed inside said palm-sized body;

a plurality of sensors to sense and output blood flow rate data of a user holding the wireless mobile phone with one of the user's hands, with the sensors being distributively disposed at a plurality of locations of the palm-sized body to facilitate having at least a subset of said sensors to contact the [holder] user's holding hand including at least one of the holding hand's finger and palm; and means disposed within said palm-sized body and coupled to the sensors to infer a manner *in which* the wireless mobile phone is being held by one of the user's hands, as characterized by the sensor contact configuration of the holding hand's finger/palm, and to generate a heart rate of the user using a subset of the blood flow rate data output by said sensors, based at least in part on the inferred hand holding manner characterized by the sensor contact configuration of the holding hand's finger/palm.

2. The wireless mobile phone of claim 1, wherein the sensors comprise a first and a second subset disposed along a first and a second edge of said palm-sized body of said wireless mobile phone to allow different subsets of said sensors to be primarily relied upon for sensing data for different potential hand holding manners of said wireless mobile phone.

3. The wireless mobile phone of claim 2, wherein said subsets comprise a first and a second subset to be primarily relied upon for sensing data for a left hand and a right hand holding manner.

4. The wireless mobile phone of claim 1, wherein said means comprises means to compare sensing data being received from said sensors against a plurality of reference characteristic profiles.

5. The wireless mobile phone of claim 1, wherein said means comprises means to select a set of weights to be applied to normalize sensing data received from said sensors.

6. The wireless mobile phone of claim 1, wherein said means comprises means to request a user to confirm a generated heart rate in a calibration mode of operation.

7. The wireless mobile phone of claim 1, wherein said means comprises a plurality of programming instructions designed to perform said inference of a hand holding manner of the wireless mobile phone and said generation of a heart rate of the user.

8. The wireless mobile phone of claim 1, wherein said means comprises circuitry for performing said inference of a hand holding manner of the wireless mobile phone and said generation of a heart rate of the user.

9. A personal digital assistant (PDA) comprising:

a palm-sized body;

memory disposed within said palm-sized body;

a processor disposed with said palm-sized body and coupled to the memory;

a plurality of sensors to sense and output blood flow rate data of a user holding the PDA with one of the user's hands, with the sensors being distributively disposed at a plurality of locations of the palm-sized body to facilitate having at least a subset of said sensors to contact the [holder] user's holding hand including at least one of the holding hand's finger and palm; and means disposed within said palm-sized body and coupled to the sensors to infer a manner [of] *in which* the PDA is being held by one of the user's hand, as characterized by the sensor contact configuration of the holding hand's finger/palm, and to generate a heart rate of the user using a subset of the blood flow rate data output by said sensors, based at least in part on the inferred hand holding manner characterized by the holding hand's finger/palm configuration characterized by the sensor contact configuration of the holding hand's finger/palm.

10. The PDA of claim 9, wherein the sensors comprise a first and a second subset disposed along a first and a second edge of said palm-sized body of said PDA to allow different subsets of said sensors to be primarily relied upon for sensing data for different potential hand holding manners of said PDA.

11. The PDA of claim 10, wherein said subsets comprise a first and a second subset to be primarily relied upon for sensing data for a left hand and a right hand holding manner.

12. The PDA of claim 9, wherein said means comprises means to compare sensing data being received from said sensors against a plurality of-reference characteristic profiles.

13. The PDA of claim 9, wherein said means comprises means to select a set of weights to be applied to normalize sensing data received from said sensors.

14. The PDA of claim 9, wherein said means comprises means to request a user to confirm a generated heart rate in a calibration mode of operation.

15. The PDA of claim 9, wherein said means comprises a plurality of programming instructions designed to perform said inference of a hand holding manner of the PDA and said generation of a heart rate of the user.

16. The PDA of claim 9, wherein said means comprises circuitry for performing said inference of a hand holding manner of the PDA and said generation of a heart rate of the user.

17. A mobile client device comprising:

a palm-sized body;

a plurality of sensors to sense and output blood flow rate data of a user holding the mobile client device with one of the user's hands, with the sensors being distributively disposed at a plurality of locations of the palm-sized body to facilitate having at least a subset of said sensors to be in contact with the [holder] user's holding hand including at least one of the holding hand's finger and palm; and means disposed within said palm-sized body and coupled to the sensors to infer a manner *in which* the mobile client device is being held by one of the user's hands, as characterized by the sensor contact configuration of the holding hand's finger/palm, and to generate a heart rate of the user using a subset of the blood flow rate data output by said sensors, based at least in part on the inferred hand holding manner characterized by the sensor contact configuration of the holding hand's finger/palm.

18. The mobile client device of claim 17, wherein the sensors comprise a first and a second subset disposed along a first and a second edge of said palm-sized body of said mobile client device to allow different subsets of said sensors to be primarily relied upon for sensing data for different potential hand holding manners of said mobile client device.

19. The mobile client device of claim 17, wherein said means comprises means to compare sensing data being received from said sensors against a plurality of reference sensing data profiles.

20. The mobile client device of claim 17, wherein said means comprises means to select a set of weights to be applied to normalize sensing data received from said sensors.

21. A mobile client device comprising:

a palm-sized body;

a plurality of sensors to sense and output bio-metric data of a user holding the mobile client device with one of the user's hands, with the sensors being distributively disposed at a plurality of locations of the palm-sized body to facilitate having at least a subset of said sensors to be in contact with the [holder] user's holding hand including at least one of the holding hand's finger and palm; and means disposed within said palm-sized body and coupled to the sensors to infer a manner *in which* the mobile client device is being held by one of the user's hands, as characterized by the sensor contact configuration of the holding hand's finger/palm, and to generate measurement of at least one bio-metric of the user using a subset of the bio-metric data output by said sensors, based at least in part on the inferred hand holding manner characterized by the sensor contact configuration of the holding hand's finger/palm.

22. The mobile client device of claim 21, wherein the sensors comprise a first and a second subset disposed along a first and a second edge of said palm-sized body of said mobile client device to allow different subsets of said sensors to be primarily relied upon for sensing data for different potential hand holding manners of said mobile client device.

23. The mobile client device of claim 21, wherein said means comprises means to compare sensing data being received from said sensors against a plurality of reference sensing data profiles.

24. The mobile client device of claim 21, wherein said means comprises means to select a set of weights to be applied to normalize sensing data received from said sensors.

*25. A portable electronic device comprising:*

*a plurality of sensors configured to sense biometric data from one or more fingers and/or a palm of a hand of a user holding the portable electronic device; and*

*a monitor coupled to the plurality of sensors to infer a manner in which the portable electronic device is held by the user as indicated by a sensor contact configuration of the user's one or more fingers and/or palm of a hand and to output a biometric of the user based at least in part on the sensed biometric data and the inferred manner in which the portable electronic device is held by the user.*

*26. The portable electronic device of claim 25, wherein the plurality of sensors are disposed along a first and a second edge of a body of the portable electronic device.*

*27. The portable electronic device of claim 25, wherein the monitor is configured to output a biometric of the user based on different subsets of the plurality of sensors detecting whether a right hand and/or left hand is holding the device.*

*28. The portable electronic device of claim 25, wherein the monitor is adapted to compare the sensed biometric data against a plurality of reference characteristic profiles.*

*29. The portable electronic device of claim 25, wherein the monitor is adapted to select and/or apply a set of weights to normalize the sensed biometric data.*

*30. The portable electronic device of claim 25, wherein the biometric data comprises blood flow related data.*

*31. The portable electronic device of claim 25, wherein the biometric comprises a heart rate.*

*32. The portable electronic device of claim 25, wherein the portable electronic device comprises a wireless mobile phone and/or a personal digital assistant.*

*33. A method comprising:*

*sensing biometric data from one or more fingers and/or a palm of a hand of a user holding a portable electronic device;*

*inferring a manner in which the portable electronic device is held by the user as indicated by a sensor contact configuration of the user's one or more fingers and/or palm of a hand; and*

*outputting on the portable electronic device a biometric of the user based at least in part on the sensed biometric data and the inferred manner in which the portable electronic device is held by the user.*

*34. The method of claim 33, further comprising determining if the device is being held by the right hand and/or left hand of the user.*

*35. The method of claim 33, wherein the method further comprises comparing the sensed biometric data against a plurality of reference characteristic profiles.*

*36. The method of claim 33, wherein the method further comprises selecting and/or applying a set of weights to normalize the sensed biometric data.*

*37. The method of claim 33, wherein the biometric data comprises blood flow related data.*

*38. The method of claim 33, wherein the biometric comprises a heart rate.*

*39. The method of claim 33, wherein the portable electronic device comprises a wireless mobile phone and/or a personal digital assistant.*

* * * * *